(12) United States Patent
Jones et al.

(10) Patent No.: US 10,046,783 B2
(45) Date of Patent: Aug. 14, 2018

(54) SHOPPING CART DEFLECTION MEASUREMENT SYSTEM AND ASSOCIATED METHODS

(71) Applicant: Wal-Mart Stores, Inc., Bentonville, AR (US)

(72) Inventors: Nicholaus Adam Jones, Fayetteville, AR (US); Robert James Taylor, Rogers, AR (US); Aaron James Vasgaard, Fayetteville, AR (US); Matthew Allen Jones, Bentonville, AR (US)

(73) Assignee: Walmart Apollo, LLC, Bentonville, AR (US)

(*) Notice: Subject to any disclaimer, the term of this patent is extended or adjusted under 35 U.S.C. 154(b) by 0 days.

(21) Appl. No.: 15/672,843

(22) Filed: Aug. 9, 2017

(65) Prior Publication Data

US 2018/0072336 A1    Mar. 15, 2018

Related U.S. Application Data

(60) Provisional application No. 62/393,231, filed on Sep. 12, 2016.

(51) Int. Cl.
*B62B 3/14*    (2006.01)
*B62B 5/00*    (2006.01)
(Continued)

(52) U.S. Cl.
CPC ............ *B62B 3/1488* (2013.01); *A47F 9/045* (2013.01); *G07G 3/003* (2013.01); *B62B 5/00* (2013.01); *G08B 13/1481* (2013.01)

(58) Field of Classification Search
CPC ........... B62B 3/14; B62B 3/1488; B62B 5/00; B62B 5/0096; A47F 9/045; G07G 3/003; G08B 13/1481
(Continued)

(56) References Cited

U.S. PATENT DOCUMENTS 3,716,697 A    2/1973  Weir
4,327,819 A *  5/1982  Coutta .................. G07G 3/003
                                                186/62

(Continued)

OTHER PUBLICATIONS

International Search Report and Written Opinion from related international patent application No. PCT/US2017/046042 dated Oct. 19, 2017.

*Primary Examiner* — John D Walters
(74) *Attorney, Agent, or Firm* — McCarter & English, LLP; David R. Burns

(57) ABSTRACT

A shopping cart deflection measurement system and associated methods are described. The shopping cart deflection measurement system includes a shopping cart, a sensor, and a processing device equipped with a processor. The shopping cart includes a frame, a basket portion pivotably mounted to the frame so as to enable deflection of at least one edge of the basket portion downward in the direction of gravity following a weight being placed in the basket portion, and a lower rack portion mounted to the frame and disposed below the basket portion. The processing device can be configured to execute instructions to measure deflection of the basket portion relative to the lower rack portion of the shopping cart using data acquired by the sensor. The measured deflection can be indicative of a fullness of the basket portion with one or more products.

20 Claims, 10 Drawing Sheets

(51) Int. Cl.
*A47F 9/04* (2006.01)
*G07G 3/00* (2006.01)
*G08B 13/14* (2006.01)

(58) Field of Classification Search
USPC .................................. 280/33.991, 33.992
See application file for complete search history.

(56) References Cited

U.S. PATENT DOCUMENTS

| | | | |
|---|---|---|---|
| 4,723,118 A | 2/1988 | Hooley et al. | |
| 4,725,822 A * | 2/1988 | Hooley | A47F 9/045 |
| | | | 186/62 |
| 7,090,230 B2 * | 8/2006 | O'Quin | B62B 3/14 |
| | | | 280/33.991 |
| 7,242,300 B1 * | 7/2007 | Konstad | A47F 9/045 |
| | | | 280/33.992 |
| 7,839,284 B2 | 11/2010 | Rosebush | |
| 7,920,062 B1 | 4/2011 | Konstad et al. | |
| 8,979,115 B1 * | 3/2015 | Baron | B62B 3/027 |
| | | | 280/43 |
| 9,473,747 B2 * | 10/2016 | Kobres | G06Q 30/00 |
| 2002/0135145 A1 | 9/2002 | Saccani | |
| 2006/0049590 A1 | 3/2006 | O'Quin | |
| 2006/0290494 A1 | 12/2006 | O'Brien | |
| 2012/0143655 A1 * | 6/2012 | Sunaoshi | G06Q 10/06395 |
| | | | 705/7.41 |
| 2014/0108252 A1 * | 4/2014 | Itwaru | G06Q 20/202 |
| | | | 705/44 |
| 2015/0029339 A1 | 1/2015 | Kobres et al. | |
| 2015/0206121 A1 * | 7/2015 | Joseph | G06Q 20/208 |
| | | | 705/23 |

* cited by examiner

SHOPPING CART DEFLECTION MEASUREMENT SYSTEM AND ASSOCIATED METHODS

CROSS-REFERENCE TO RELATED APPLICATIONS

This application claims the benefit of commonly assigned U.S. Provisional Patent Application No. 62/393,231, which was filed on Sep. 12, 2016. The entire content of the foregoing provisional patent application is incorporated herein by reference.

BACKGROUND

Some retail environments provide an electronic device to customers to scan products as the customer places products into a shopping cart. Such devices allow the retail environment to collect information regarding movement of customers within the retail environment, as well as the products being purchased and the time of the purchase. However, such electronic devices generally require a significant amount of infrastructure, device maintenance, and data management, resulting in overall increased costs of management.

SUMMARY

Exemplary embodiments of the present invention provide a shopping cart deflection measurement system that allows for real-time (or substantially real-time) monitoring of customer activity within a retail environment. In particular, by measuring deflection of a basket portion of the shopping cart relative to a lower rack, a determination of a fullness of the basket portion with one or more products can be determined. In some embodiments, the exemplary shopping cart deflection measurement system can be used as a security feature to detect whether all items have been removed from the basket portion of the shopping cart and placed on a belt at a point-of-sale area. The system thereby monitors customer activity within the retail environment while having reduced overall costs of management of the system.

In one embodiment, an exemplary shopping cart deflection measurement system includes a shopping cart, a sensor, and a processing device equipped with a processor. The shopping cart includes a frame, a basket portion and a lower rack. The basket portion can be pivotably mounted to the frame (e.g., in a cantilever manner) so as to enable deflection of at least one edge of the basket portion downward in the direction of gravity following a weight being placed in the basket portion. The lower rack portion can be mounted to the frame and disposed below the basket portion. The processing device can be configured to execute instructions to measure deflection of the basket portion relative to the lower rack portion of the shopping cart using data acquired by the sensor. The measured deflection of the basket portion can be indicative of a fullness of the basket portion with one or more products.

In another embodiment, an exemplary non-transitory computer-readable medium is provided for determining fullness of a shopping cart. The instructions are executable by a processing device. The shopping cart includes a frame, a basket portion pivotably mounted to the frame so as to enable deflection of at least one edge of the basket portion downward in the direction of gravity following a weight being placed in the basket portion, and a lower rack portion mounted to the frame and disposed below the basket portion. Execution of the instructions by the processing device causes the processing device to receive sensor data from a sensor with respect to the basket portion. Execution of the instructions by the processing device also causes the processing device to measure deflection of the basket portion relative to the lower rack portion of the shopping cart based on the sensor data to determine fullness of the basket portion.

In an embodiment, an exemplary method of determining fullness of a shopping cart is provided. The shopping cart includes a frame, a basket portion pivotably mounted to the frame so as to enable deflection of at least one edge of the basket portion downward in the direction of gravity following a weight being placed in the basket portion, and a lower rack portion mounted to the frame and disposed below the basket portion. The method includes receiving sensor data from a sensor with respect to the basket portion. The method includes measuring deflection of the basket portion relative to the lower rack portion of the shopping cart based on the sensor data to determine fullness of the basket portion.

It should be appreciated that any combination and/or permutation of embodiments is envisioned as being within the scope of the present invention. Other objects and features will become apparent from the following detailed description considered in conjunction with the accompanying drawings. It is to be understood, however, that the drawings are designed as an illustration only and not as a definition of the limits of the present disclosure.

BRIEF DESCRIPTION OF THE DRAWINGS

To assist those of skill in the art in making and using the disclosed shopping cart deflection measurement systems and associated methods, reference is made to the accompanying figures. The accompanying figures, which are incorporated in and constitute a part of this specification, illustrate one or more embodiments of the invention and, together with the description, help to explain the invention. In the figures.

DETAILED DESCRIPTION

Exemplary embodiments of the present invention allow for real-time (or substantially real-time) monitoring of customer activity within a retail environment. In particular, an exemplary shopping cart deflection measurement system monitors additions of weight into the basket portion of the shopping cart by measuring deflection of the basket portion relative to a lower rack portion of the shopping cart. Measurement of the deflection of the basket portion is performed via one or more sensors, e.g., cameras disposed around the retail environment, a sound emitter disposed on the shopping cart and listening devices disposed around the retail environment, combinations thereof, or the like. The measured deflection is indicative of a fullness of the basket portion with one or more products collected by a customer.

Figure 1:
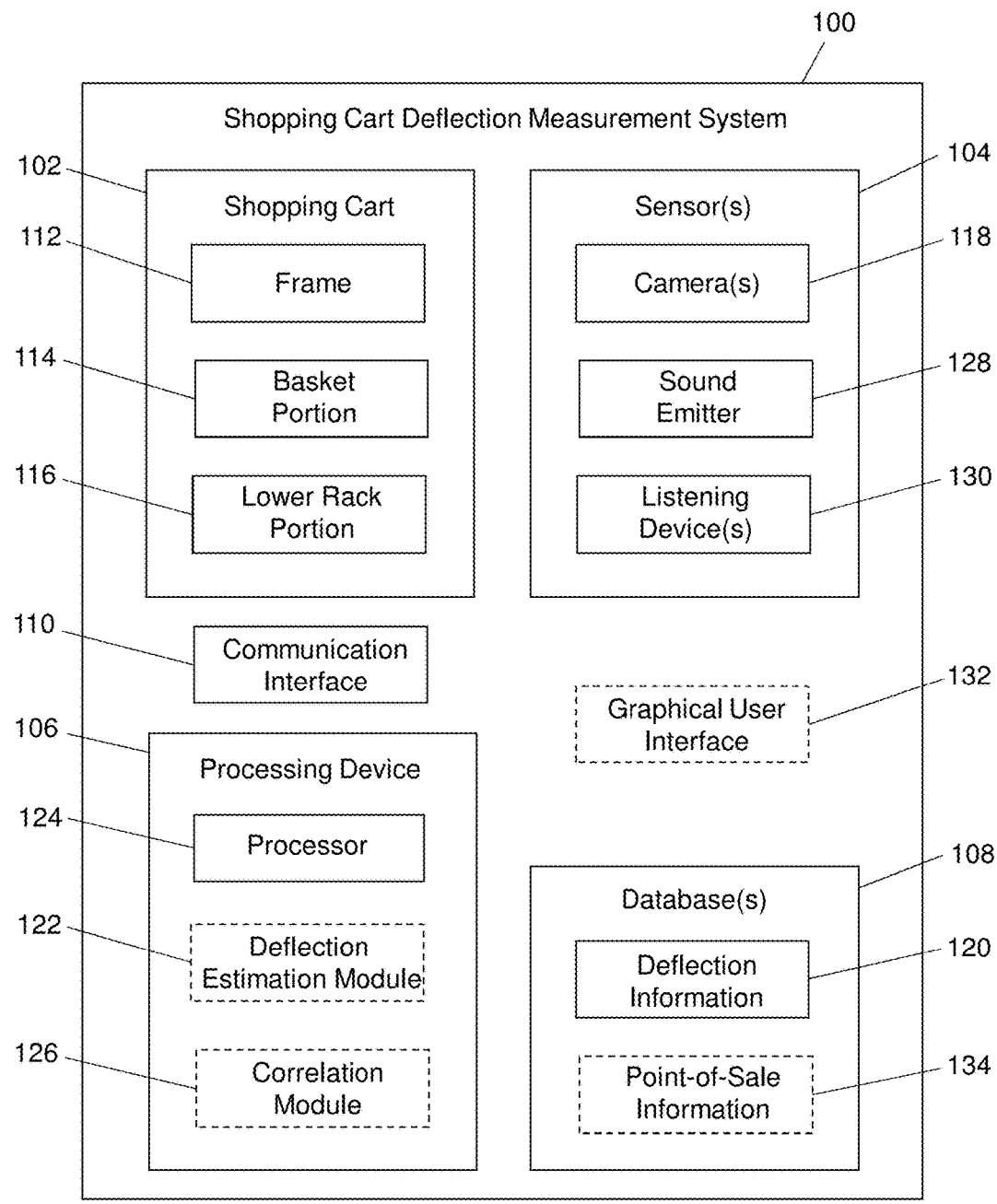
FIG. 1 is a block diagram of an exemplary shopping cart deflection measurement system in an embodiment.

FIG. 1 is a block diagram of an exemplary shopping cart deflection measurement system 100 (hereinafter "system 100") in accordance with exemplary embodiments of the present disclosure. The system 100 generally includes at least one shopping cart 102, at least one sensor 104, a processing device 106, and one or more databases 108. The system 100 also includes a communication interface 110 configured to provide wired and/or wireless communication (e.g., transmission of data) between the sensor 104, the processing device 106, and the databases 108.

The shopping cart 102 generally includes a frame 112 with a basket portion 114 and a lower rack portion 116 mounted to the frame 112. The lower rack portion 116 can be mounted to the frame 112 at a point below a bottom surface of the basket portion 114 and generally parallel to a floor surface upon which the shopping cart 102 rests. The basket portion 114 can be mounted to the frame 112 in a cantilever manner such that one end is secured to the frame 112 and the opposing end extends from the frame 112. As such, the basket portion 114 is pivotably mounted to the frame 112, allowing for deflection of at least one edge of the basket portion 112 downward in the direction of gravity and the lower rack portion 116 after a weight is placed in the basket portion 114. For example, the deflection may occur when one or more products are placed in the basket portion 114.

In an embodiment, the sensor 104 can be in the form of one or more cameras 118 disposed around the retail environment. For example, the cameras 118 can be mounted at a ceiling level and/or a wall location of the retail environment and can be configured to capture images of the shopping carts 102 on the floor of the retail environment. In particular, at least one camera 118 can be configured to capture a first image of a shopping cart 102 in which an initial height (e.g., a starting height) between the basket portion 114 and the lower rack portion 116 is measured prior to placement of weight (e.g., products) into the basket portion 114. In other words, the first image may be taken when the basket portion 114 is empty. The camera 118 can be configured to capture one or more subsequent images of the respective shopping cart 102 in which a subsequent height (e.g., a deflected height) between the basket portion 114 and the lower rack portion 116 is measured after placement of weight into the basket portion 114. In one embodiment, the shopping cart 102 may be affixed with a visible identifier by which the camera 118 may uniquely identify the specific shopping cart. In another embodiment, the shopping cart 102 may be equipped with a radio frequency identification (RFID) tag by which its location is tracked by the retail environment.

The measured heights can be transmitted via the communication interface 110 to the database 108 for storage as deflection information 120. In an embodiment, the system 100 can include a deflection estimation module 122. Although shown as executing on the processing device 106, in an embodiment, the deflection estimation module 122 can be executed on a separate processing device and the results of the execution can be forwarded to the processing device 106. A processor 124 of the processing device 106 can execute the deflection estimation module 122 to receive as input the deflection information 120 and determine a difference between the measured subsequent height and the initial height. If the subsequent height is smaller than the initial height, the deflection estimation module 122 can output an indication that one or more products have been positioned in the basket portion 114 of the shopping cart 102.

Additionally, in an embodiment, the deflection estimation module 122 can utilize a predetermined deflection scale to estimate the weight of products positioned in the basket portion 114 and the fullness of the basket portion 114. In particular, based on the amount of measured deflection of the basket portion 114 relative to the lower rack portion 116, and based on previously gathered deflection data, the deflection estimation module 122 can estimate the weight of products positioned in the basket portion 114 and the fullness of the basket portion 114. The estimated weight of the products and the fullness of the basket portion 114 can be transmitted to the database 108 via the communication interface 110 and stored in as deflection information 120. In an embodiment, the estimated weight of the products and/or the fullness of the basket portion 114 can be used to monitor customer traffic within the retail environment, and estimate when customers are completing their shopping and heading towards the point-of-sale (POS) terminals, thereby allowing the retail environment to properly staff the POS terminals in preparation for approaching customers.

In an embodiment, the system 100 can include a correlation module 126. Although shown as executing on the processing device 106, in an embodiment, the correlation module 126 can be executed on a separate processing device with the results of its execution forward to processing device 106. The correlation module 126 can be executed by the processor 124 to correlate the estimated deflection of the shopping cart 102 and the estimated fullness of the basket portion 114 with data collected at one or more POS terminals in the retail environment (e.g., POS information 134). In particular, the POS information 134 can include data on the products purchased by a customer. The POS data can be used to estimate the overall weight of the products purchased by the customer and the correlation module 126 can correlate the estimated weight of the products determined by the deflection estimation module 122 with the estimated weight based on the POS data used to determine the accuracy of the system 100. In some embodiments, the system 100 can be used as a security feature to detect whether all items have been removed from the basket portion 114 of the shopping cart 102 and placed on a belt at the POS terminal. For example, if the system 100 detects that one or more items are still in the basket portion 114 when the customer indicates a completion of checkout at the POS terminal, an audio and/or visual signal can be output to indicate that additional items remain in the basket portion 114.

In an embodiment, the sensors 104 can be in the form of a sound emitter 128 mounted on each shopping cart 102 and one or more listening devices 130 disposed around the retail environment. The sound emitter 128 can be configured to emit sounds of different frequencies (e.g., outside of the human hearing range) depending on an amount of deflection of the basket portion 114 relative to the lower rack portion 116 (and/or relative to the frame 112). In an embodiment, the sound emitter 128 can emit sounds after a predetermined period of time (e.g., every five seconds, every ten seconds, every twenty seconds, every thirty seconds, every 60 seconds, or the like). In an embodiment, the sound emitter 128 may also emit an identifier allowing the shopping cart 102 to be uniquely identified by the system 100. In another embodiment, a shopping cart 102 equipped with the sound emitter 128 may also be equipped with a visual identifier by which a camera may uniquely identify the shopping cart 102 or an RFID tag tracked by the retail environment.

The sound emitter 128 can be disposed between the basket portion 114 and the lower rack portion 116. In one embodiment, the sound emitter 128 can be disposed adjacent to a bottom surface of the basket portion 114 at the connecting point of the basket portion 114 with the frame 112. In particular, the sound emitter 128 can be disposed such that any deflection of the basket portion 114 relative to the lower rack portion 116 is immediately sensed by the sound emitter 128, thereby changing the frequency of the sound generated by the sound emitter 128. Thus, upon any change in weight within the basket portion 114, the frequency of the sound generated by the sound emitter 128 varies for each respective shopping cart 102.

The one or more listening devices 130 can be mounted around the retail environment and can be configured to detect sounds emitted from the sound emitter 128 of each shopping cart 102. The detected sounds can be transmitted to the database 108 via the communication interface 110 for storage as deflection information 120. The deflection estimation module 122 can be executed by the processor 124 to receive as input the detected sounds and, based on the frequency of the detected sounds, the deflection estimation module 122 can estimate the amount of deflection of the basket portion 114 relative to the lower rack portion 116.

In an embodiment, the estimated deflection of the basket portion 114 can be used by the deflection estimation module 122 in conjunction with a predetermined deflection scale to estimate the weight of products positioned in the basket portion 114 and the fullness of the basket portion 114. In an embodiment, the estimated weight of the products and/or the fullness of the basket portion 114 can be used to monitor customer traffic within the retail environment, and estimate when customers are completing their shopping and heading towards the POS terminals, thereby allowing the retail environment to properly staff the POS terminals in preparation for approaching customers. In an embodiment, the data generated by the system 100 based on the sound emitters 128 and the listening devices 130 can be correlated with the POS information 134 to determine the accuracy of the system 100.

In an embodiment, the shopping cart 102 can be identified based on tracking of a customer's device (e.g., a smart device). In an embodiment, the shopping cart 102 can be identified using passive sound (e.g., listening devices 130 detecting location of the shopping cart 102 as it travels within the retail environment). In an embodiment, the shopping carts 102 can be monitored when entering and leaving the retail environment to detect the cumulative change in the shopping carts 102, the cumulative change indicating the amount of products purchased at the retail environment. Such information can be used for marketing efforts (e.g., targeted marketing) in the area. In addition, such information can be used to determine which products are selling well and which products should be replaced.

The system 100 can include a graphical user interface (GUI) 132 for displaying information and/or notifications to a user associated with the retail environment. For example, the GUI 132 can be on a personal computer and/or a mobile smart device, and can notify the user of customer traffic patterns within the retail environment, the average weight of products being purchased by customers, combinations thereof, or the like.

Figure 2:
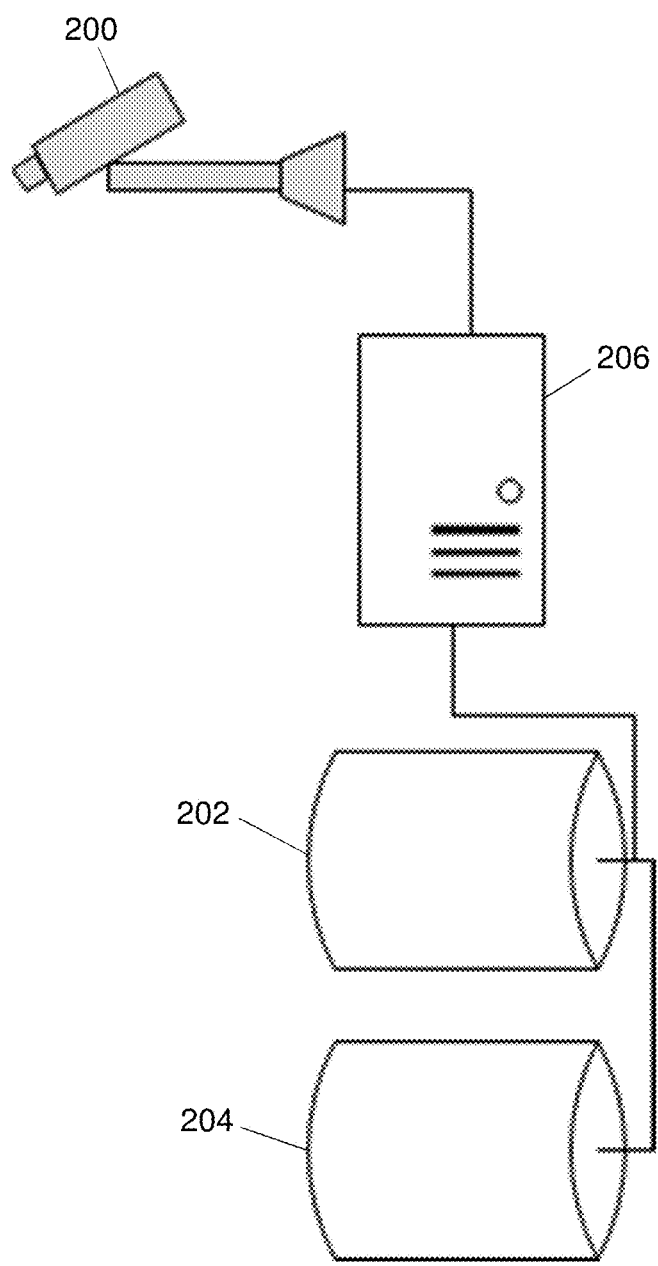
FIG. 2 is a block diagram of an exemplary implementation of a sensor of a shopping cart deflection measurement system in an embodiment.

FIG. 2 is a block diagram of an exemplary implementation of a sensor 200 of the system 100. The sensor 200 can be in the form of one or more cameras disposed around the retail environment. The sensor 200 can be communicatively connected to a shopping cart loading database 202 and a POS database 204 via server 206. The shopping cart loading database 202 can include information for each shopping cart relating to the measured deflection of the basket portion 114 relative to the lower rack portion 116, including the measured initial and subsequent heights. The POS database 204 can include information relating to the product weight sold per hour at the POS terminals.

Figure 3:
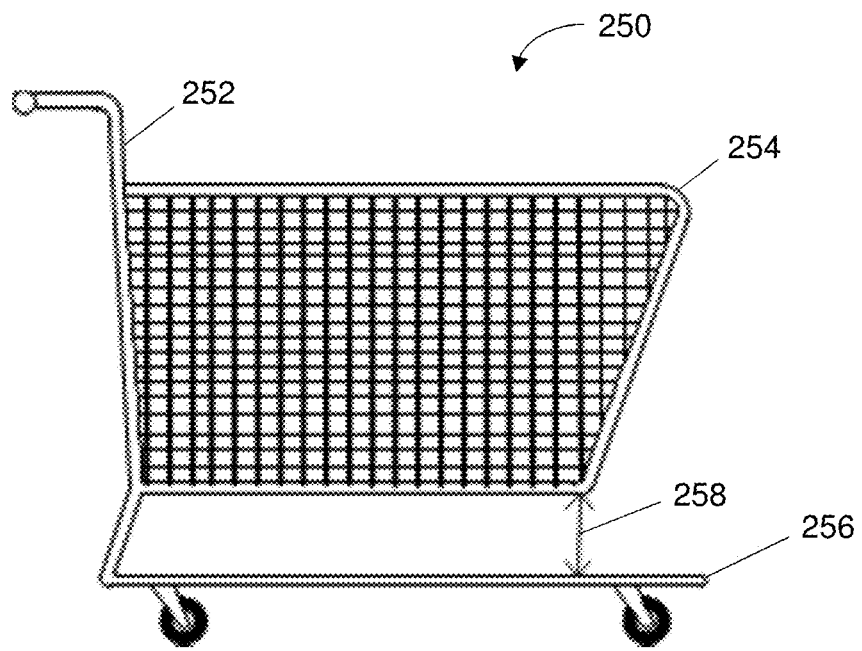
FIG. 3 is a diagram of a shopping cart of an exemplary shopping cart deflection measurement system in a non-deflected position in an embodiment.
Figure 4:
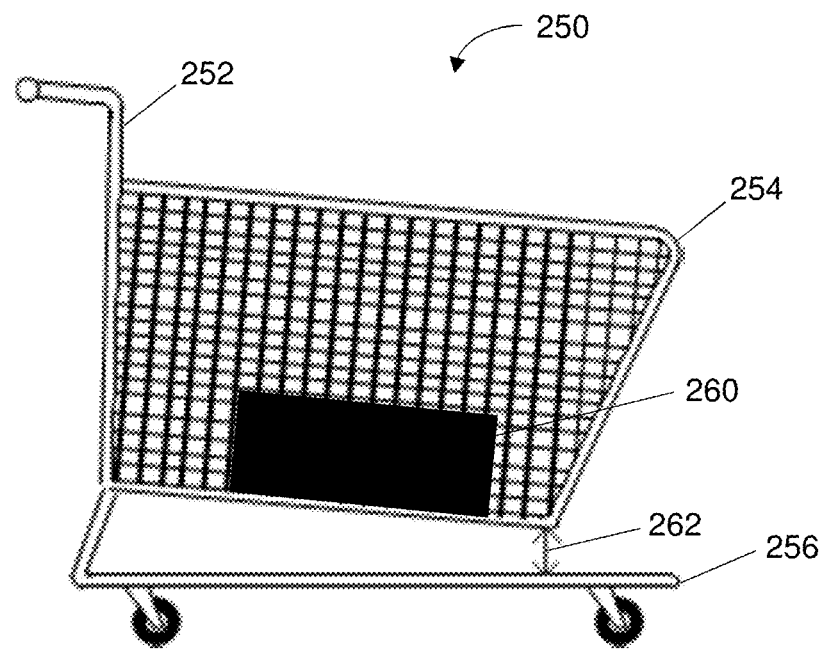
FIG. 4 is a diagram of a shopping cart of an exemplary shopping cart deflection measurement system in a deflected position in an embodiment.

FIGS. 3 and 4 show diagrams of a shopping cart 250 of the system 100 in a non-deflected position and a deflected position, respectively. As discussed above, the shopping cart 250 includes a frame 252, a basket portion 254, and a lower rack portion 256 disposed below the basket portion 254. The one or more cameras of the system 100 can capture one or more images of the shopping cart 250 with the basket portion 254 at the initial height 258 relative to the lower rack portion 256. In particular, the initial height 258 represents the basket portion 254 in a non-deflected (empty) position before any products have been positioned in the basket portion 254.

FIG. 4 shows the shopping cart 250 with a product 260 disposed within the basket portion 254. Due to the weight of the product 260, the basket portion 254 has deflected downward in the direction of gravity and in the direction of the lower rack portion 256. The one or more cameras can capture one or more images of the shopping cart 250 with the basket portion 254 at a subsequent height 262 (i.e., a deflected height) above the lower rack portion 256. The difference between the subsequent height 262 and the initial height 258 can be processed by the deflection estimation module 122 to estimate the amount of deflection of the basket portion 254, the weight of product(s) positioned in the basket portion 254, and/or the fullness of the basket portion 254.

Figure 5:
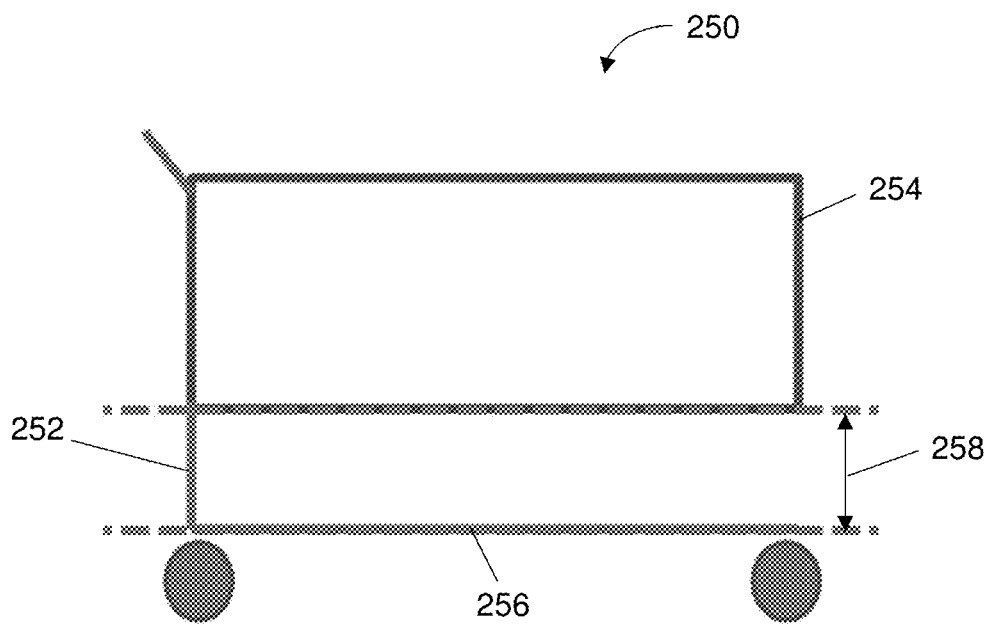
FIG. 5 is a diagram of a shopping cart of an exemplary shopping cart deflection measurement system in a non-deflected position in an embodiment.
Figure 6:
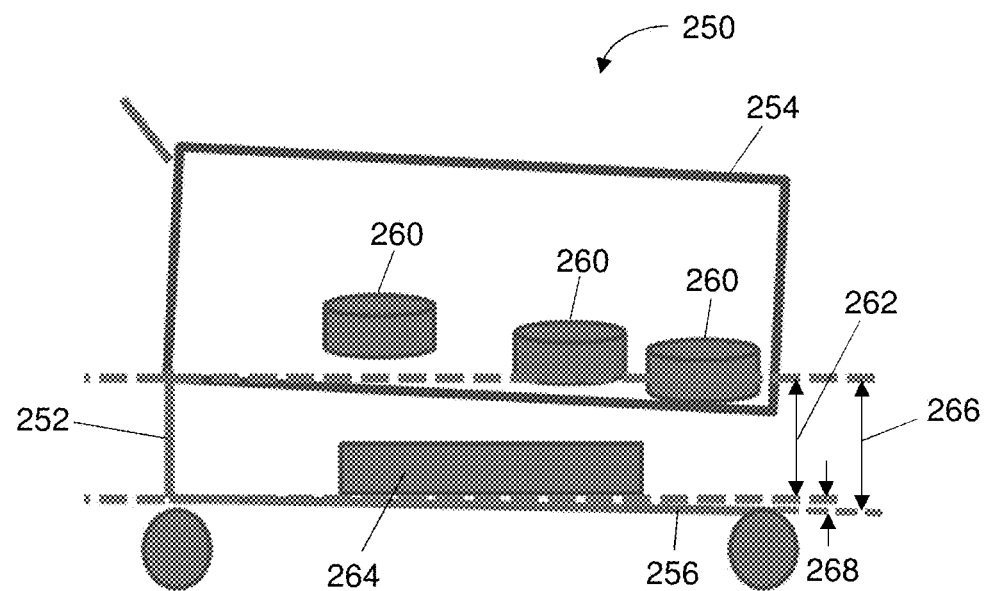
FIG. 6 is a diagram of a shopping cart of an exemplary shopping cart deflection measurement system in a deflected position in an embodiment.

FIGS. 5 and 6 show diagrams of a shopping cart 250 of the system in a non-deflected position and a deflected position, respectively. FIG. 5 is substantially similar in structure to the shopping cart of FIG. 3, including the initial height 258 between the bottom surface of the basket portion 254 and the top surface of the lower rack portion 256. FIG. 6 shows the basket portion 254 loaded with three products 260. In addition, FIG. 6 shows the lower rack portion 256 loaded with a product 264. Due to the weight of the products 260, the basket portion 254 deflects downward in the direction of gravity and the lower rack portion 256. Due to the weight of the product 264, the lower rack portion 256 also deflects downward in the direction of gravity.

In an embodiment, based on one or more images captured by the camera, the deflection estimation module 122 can estimate the amount of deflection of the basket portion 254 relative to the initial position of the lower rack portion 256 (e.g., subsequent height 262). In an embodiment, based on one or more images captured by the camera, the deflection estimation module 122 can estimate the amount of deflection of the basket portion 254 relative to the deflected position of the lower rack portion 256 (e.g., subsequent height 266). In an embodiment, based on one or more images captured by the camera, the deflection estimation module 122 can estimate the amount of deflection of the lower rack portion 256 relative to the initial position of the lower rack portion 256 (e.g., subsequent height 268), thereby taking into account the weight of the product 264 and the fullness of the lower rack portion 256. In an embodiment, each of the subsequent heights 262, 266, 268 can be estimated and stored in the database 108.

In an embodiment, the shopping cart 250 deflection can be measured with networked cameras, and a correlation can be determined between the weight of products purchased at the POS terminals and the deflection of each shopping cart 250. The system 100 can store the weight of products purchased by customers at the POS terminals and the estimated deflection of the shopping carts 250 by time (e.g., by each hour) and day. In an embodiment, the stored data can become a metric to be used by the retail environment for properly staffing associates for assistance in the aisles of the retail environment and/or at the POS terminals.

Figure 7:
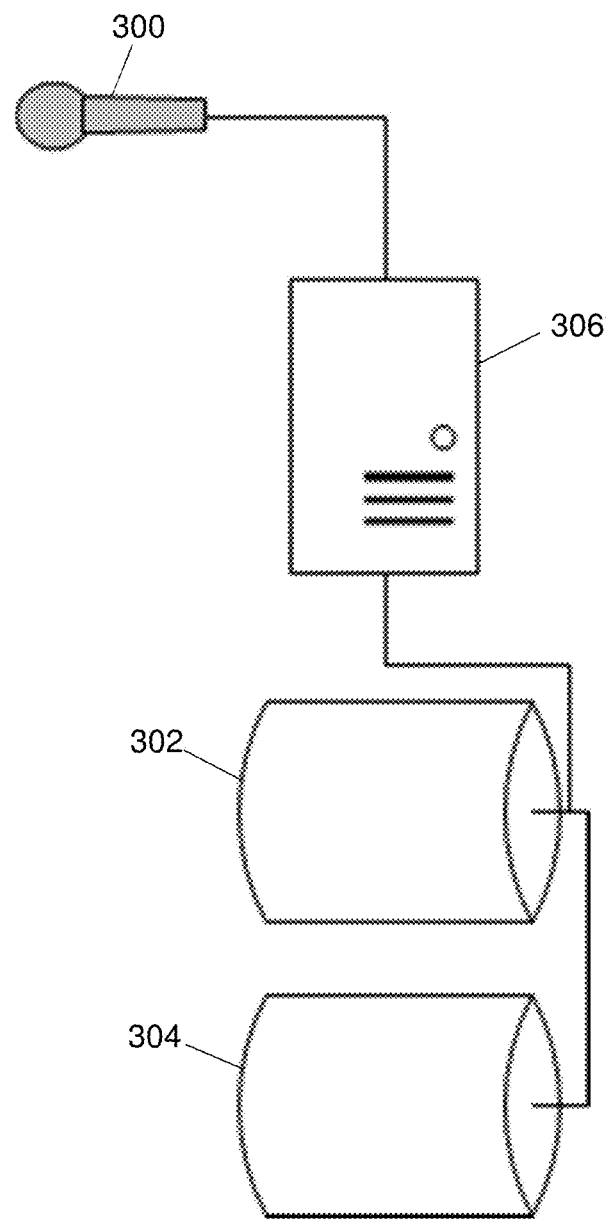
FIG. 7 is a block diagram of an exemplary implementation of a sensor of a shopping cart deflection measurement system in an embodiment.

FIG. 7 is a block diagram of an exemplary implementation of a sensor 300 of the system 100. The sensor 300 can be in the form of one or more listening devices disposed around the retail environment and configured to detect signals from a sound emitter mounted to the respective shopping carts 102 (see, e.g., FIG. 8). The sensor 300 can be communicatively connected to a shopping cart loading database 302 and a POS database 304 via server 306. The shopping cart loading database 302 can include information relating to the detected sounds emitted from the sound emitter mounted on the respective shopping carts 102, including the correlation between the frequency of the detected sound and the deflection of the basket portion 114 relative to the lower rack portion 116. The POS database 304 can include information relating to the product weight sold per hour at the POS terminals.

Figure 8:
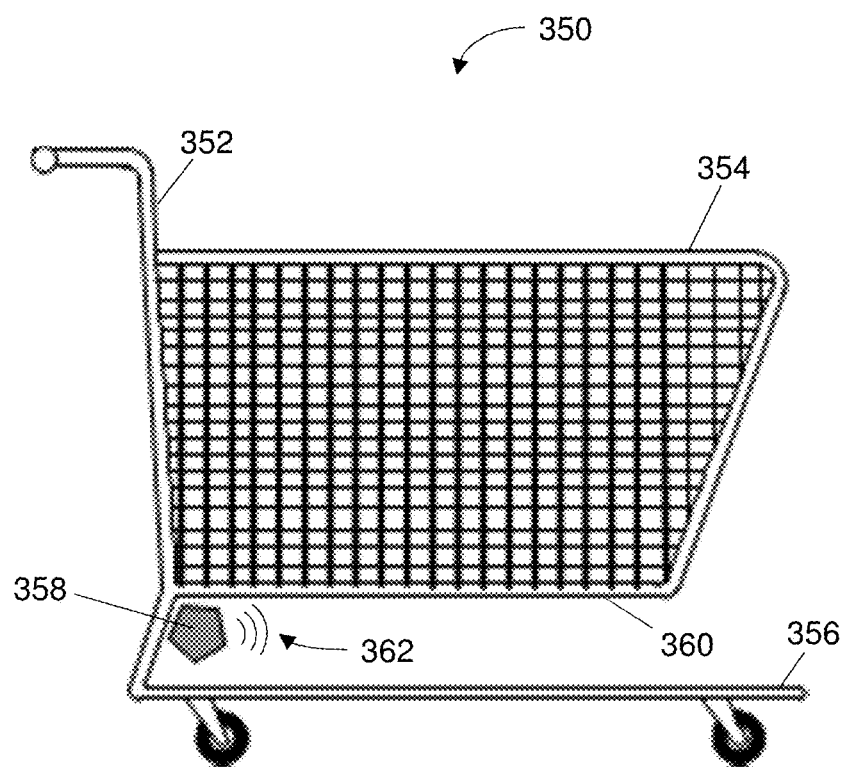
FIG. 8 is a diagram of a shopping cart of an exemplary shopping cart deflection measurement system including a sound emitter in an embodiment.

FIG. 8 shows a diagram of a shopping cart 350 of the system 100 in a non-deflected position. As discussed above, the shopping cart 350 includes a frame 352, a basket portion 354, and a lower rack portion 356 disposed below the basket portion 354. As part of the sensor system associated with the system 100, the shopping cart 350 can include a sound emitter 358 mounted to the shopping cart 350. In an embodiment, the sound emitter 358 can be mounted to the frame 352 directly below a bottom surface 360 of the basket portion 354. In an embodiment, the sound emitter 358 can be mounted to the frame 352 and to the bottom surface 360 of the basket portion 354. It will be appreciated that other locations of the sound emitter 358, in addition to, or in combination with, those specifically described herein are also considered to be within the scope of the present invention.

In particular, the sound emitter 358 is mounted to the shopping cart 350 such that any deflection of the basket portion 354 in the direction of gravity and the lower rack portion 356 due to weight placed into the basket portion 354 causes the sound emitter 358 to emit a sound 362 of a different frequency than when the basket portion 354 is empty. For example, in one embodiment, the sound emitter 358 may be in mechanical communication with the joint between the bottom surface of the basket portion 354 and the frame 352 such that the sound emitter 358 detects changes in an angle where the two surfaces meet and thus receives an indication of the degree of deflection. Further, the sound emitter 358 can be configured to emit sounds 362 at different frequencies (e.g., a wide range of frequencies) based on the amount of deflection of the basket portion 354 relative to the lower rack portion 356. In an embodiment, the shopping cart 350 can include an additional sound emitter 358 disposed adjacent and/or below the lower rack portion 356 to emit sounds 362 of different frequencies based on deflection of the lower rack portion 356 relative to the frame 352.

It should be understood that the sound emitter 358 can emit sounds 362 of a certain frequency when the shopping cart 350 is empty, and the emitted sounds 362 vary based on the amount of deflection of the basket portion 354 relative to the lower rack portion 356. The emitted sounds 362 can be detected by one or more listening devices 300 (see, e.g., FIG. 7). Based on the frequency of the emitted sound 362, the listening device 300 (and/or the processing device 106) can correlate the emitted sound 362 with the amount of deflection of the basket portion 354. Based on the estimated deflection of the basket portion 354, an estimation of the weight of the products in the basket portion 354 and the fullness of the basket portion 354 can be determined. In an embodiment, the features of the shopping cart 350 can be incorporated with the features discussed relative to the shopping cart 250.

In an embodiment, the shopping cart 350 deflection can be measured with networked listening devices, and a correlation can be determined between the weight of products purchased at the POS terminals and the deflection of each shopping cart 350. The system 100 can store the weight of products purchased by customers at the POS terminals and store the estimated deflection of the shopping carts 350 by time (e.g., by each hour) and day. In an embodiment, the stored data can become a metric to be used by the retail environment for properly staffing associates for assistance in the aisles of the retail environment and/or at the POS terminals. In an embodiment, multiple listening devices can be configured to detect the sounds 362 emitted from the same sound emitter 358, and triangulation methods can be implemented to determine the location of the shopping cart 350 in the retail environment.

Figure 9:
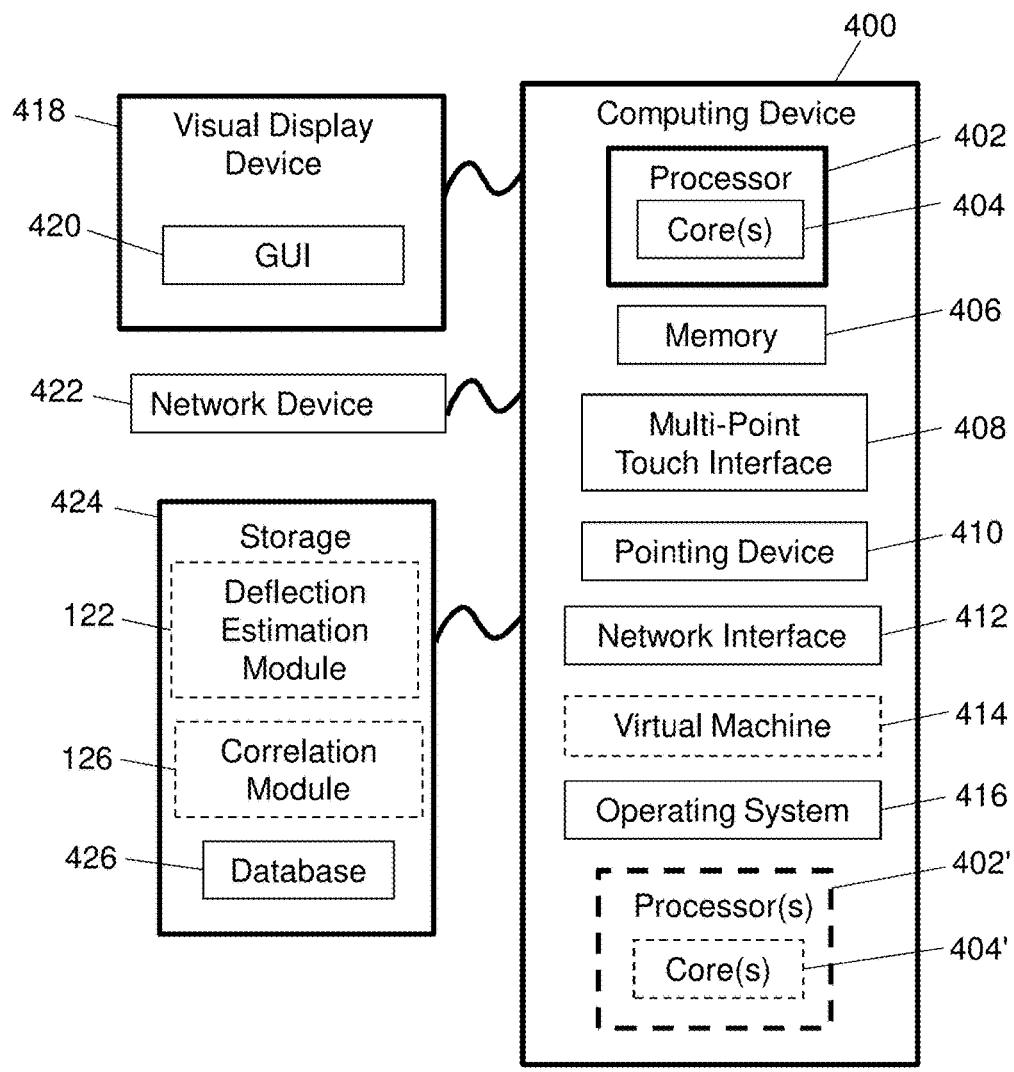
FIG. 9 is a block diagram of a computing device in accordance with exemplary embodiments in an embodiment.

FIG. 9 is a block diagram of a computing device 400 in accordance with exemplary embodiments of the present disclosure. The computing device 400 includes one or more non-transitory computer-readable media for storing one or more computer-executable instructions or software for implementing exemplary embodiments. The non-transitory computer-readable media may include, but are not limited to, one or more types of hardware memory, non-transitory tangible media (for example, one or more magnetic storage disks, one or more optical disks, one or more flash drives), and the like. For example, memory 406 included in the computing device 400 may store computer-readable and computer-executable instructions or software for implementing exemplary embodiments of the present disclosure (e.g., instructions for executing the deflection estimation module 122, the correlation module 126, combinations thereof, or the like). The computing device 400 also includes configurable and/or programmable processor 402 and associated core 404, and optionally, one or more additional configurable and/or programmable processor(s) 402' and associated core(s) 404' (for example, in the case of computer systems having multiple processors/cores), for executing computer-readable and computer-executable instructions or software stored in the memory 406 and other programs for controlling system hardware. Processor 402 and processor(s) 402' may each be a single core processor or multiple core (404 and 404') processor.

Virtualization may be employed in the computing device 400 so that infrastructure and resources in the computing device 400 may be shared dynamically. A virtual machine 414 may be provided to handle a process running on multiple processors so that the process appears to be using only one computing resource rather than multiple computing resources. Multiple virtual machines may also be used with one processor.

Memory 406 may include a computer system memory or random access memory, such as DRAM, SRAM, EDO RAM, and the like. Memory 406 may include other types of memory as well, or combinations thereof.

A user may interact with the computing device 400 through a visual display device 418 (e.g., a personal computer, a mobile smart device, or the like), such as a computer monitor, which may display one or more user interfaces 420 (e.g., GUI 132) that may be provided in accordance with exemplary embodiments. The computing device 400 may include other I/O devices for receiving input from a user, for example, a keyboard or any suitable multi-point touch interface 408, a pointing device 410 (e.g., a mouse). The keyboard 408 and the pointing device 410 may be coupled to the visual display device 418. The computing device 400 may include other suitable conventional I/O peripherals.

The computing device 400 may also include one or more storage devices 424, such as a hard-drive, CD-ROM, or other computer readable media, for storing data and computer-readable instructions and/or software that implement exemplary embodiments of the deflection estimation module 122, the correlation module 126, combinations thereof, or the like, described herein. Exemplary storage device 424 may also store one or more databases 426 for storing any suitable information required to implement exemplary embodiments. For example, exemplary storage device 424 can store one or more databases 426 for storing information, such as data relating to the deflection information 120, the POS information 134, or the like, and computer-readable instructions and/or software that implement exemplary embodiments described herein. The databases 426 may be updated by manually or automatically at any suitable time to add, delete, and/or update one or more items in the databases.

The computing device 400 can include a network interface 412 configured to interface via one or more network devices 422 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 412 may include a built-in network adapter, network interface card, PCMCIA network card, card bus network adapter, wireless network adapter, USB network adapter, modem or any other device suitable for interfacing the computing device 400 to any type of network capable of communication and performing the operations described herein. Moreover, the computing device 400 may be any computer system, such as a workstation, desktop computer, server, laptop, handheld computer, tablet computer (e.g., the iPad™ tablet computer), mobile computing or communication device (e.g., the iPhone™ communication device), or other form of computing or telecommunications device that is capable of communication and that has sufficient processor power and memory capacity to perform the operations described herein.

The computing device 400 may run any operating system 416, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, or any other operating system capable of running on the computing device and performing the operations described herein. In exemplary embodiments, the operating system 416 may be run in native mode or emulated mode. In an exemplary embodiment, the operating system 416 may be run on one or more cloud machine instances.

Figure 10:
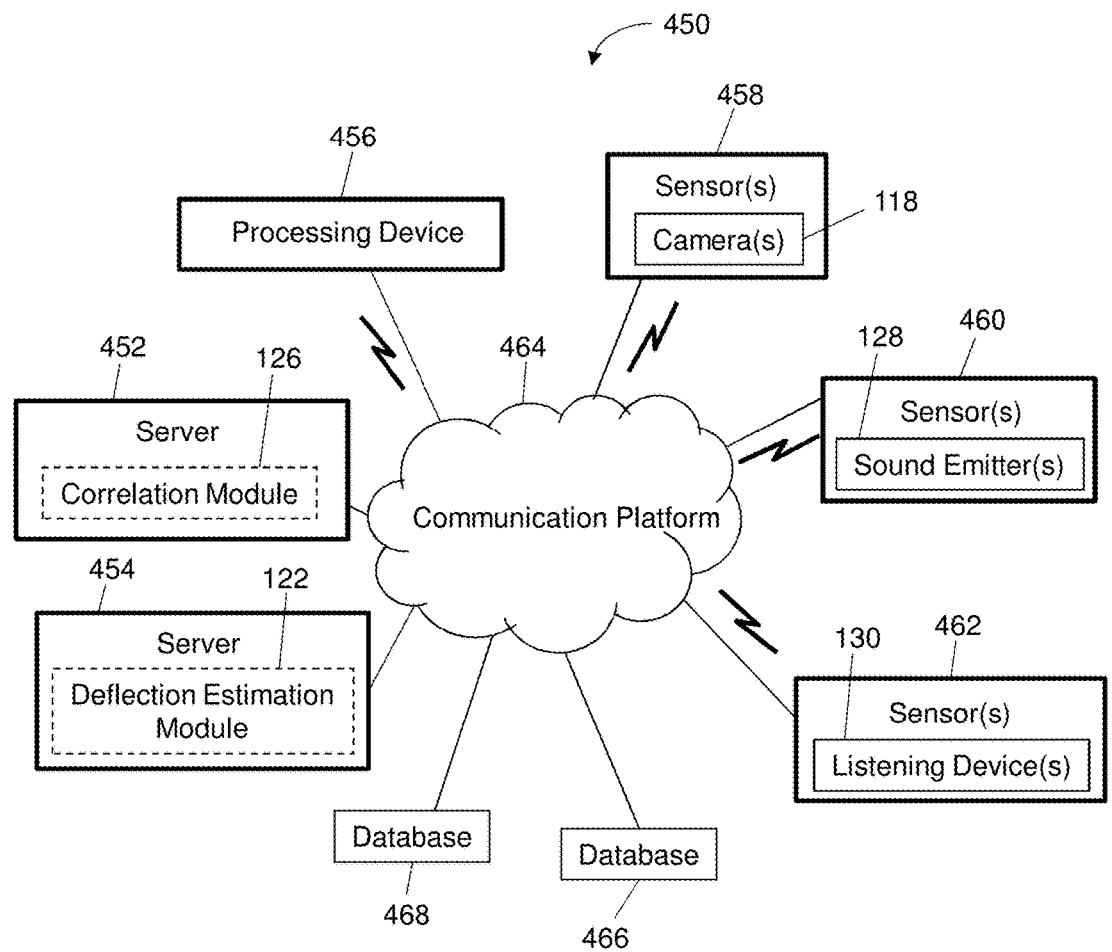
FIG. 10 is a block diagram of an exemplary shopping cart deflection measurement system environment in accordance with an embodiment.

FIG. 10 is a block diagram of an exemplary shopping cart deflection measurement system environment 450 in accordance with exemplary embodiments of the present disclosure. The environment 450 can include servers 452, 454 operatively coupled to a processing device 456, and sensors 458, 460, 462, via a communication platform 464, which can be any network over which information can be transmitted between devices communicatively coupled to the network. For example, the communication platform 464 can be the Internet, Intranet, virtual private network (VPN), wide area network (WAN), local area network (LAN), and the like. In an embodiment, the communication platform 464 can be part of a cloud environment. The environment 450 can include repositories or databases 466, 468, which can be operatively coupled to the servers 452, 454, as well as to the processing device 456 and the sensors 458, 460, 462, via the communications platform 464. In exemplary embodiments, the servers 452, 454, processing device 456, sensors 458, 460, 462, and databases 466, 468 can be implemented as computing devices (e.g., computing device 400). Those skilled in the art will recognize that the databases 466, 468 can be incorporated into one or more of the servers 452, 454 such that one or more of the servers 452, 454 can include databases 466, 468. In an embodiment, the database 466 can store the deflection information 120, and the database 468 can store the POS information 134. In an embodiment, a single database 466, 468 can store both the deflection information 120 and the POS information 134.

In an embodiment, embodiments of the servers 452, 454 can be configured to implement one or more portions of the system 100. For example, server 452 can be configured to implement one or more portions of the correlation module 126. As a further example, server 454 can be configured to implement one or more portions of the deflection estimation module 122.

In an embodiment, the sensors 458 can be in the form of one or more cameras 118 disposed throughout the retail environment. In an embodiment, the sensors 360 can be in the form of one or more sound emitters 128 mounted to respective shopping carts 102 and one or more listening devices 130 disposed throughout the retail environment.

Figure 11:
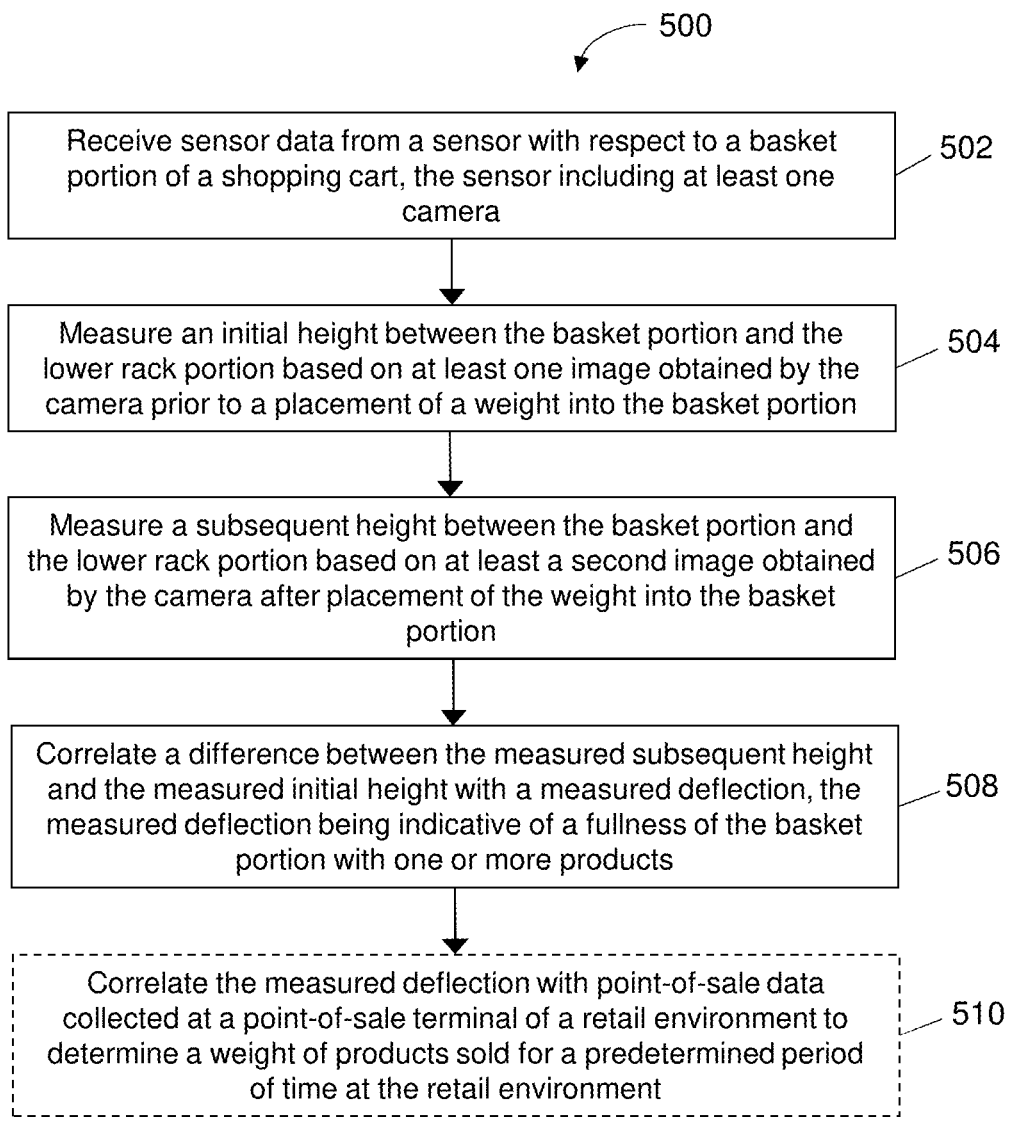
FIG. 11 is a flowchart illustrating an implementation of an exemplary shopping cart deflection measurement system in accordance with an embodiment.

FIG. 11 is a flowchart illustrating an exemplary process 500 as implemented by the shopping cart deflection measurement system 100 in an embodiment that includes sensors in the form of cameras. To begin, at step 502, sensor data is received from one or more cameras with respect to a basket portion of a shopping cart. At step 504, an initial height between the basket portion and the lower rack portion can be measured based on at least one image in the sensor data obtained by the one or more cameras prior to a placement of a weight (e.g., one or more products) into the basket portion. At step 506, a subsequent height between the basket portion and the lower rack portion can be measured based on at least one second image obtained by the one or more cameras after placement of the weight into the basket portion. At step 508, a difference between the measured subsequent height and the measured initial height can be correlated with a measured deflection, the measured deflection being indicative of a fullness of the basket portion with one or more products. Optionally, at step 510, the measured deflection can be correlated with POS data collected at a POS terminal of the retail environment to determine the weight of products sold for a predetermined period of time at the retail environment.

Figure 12:
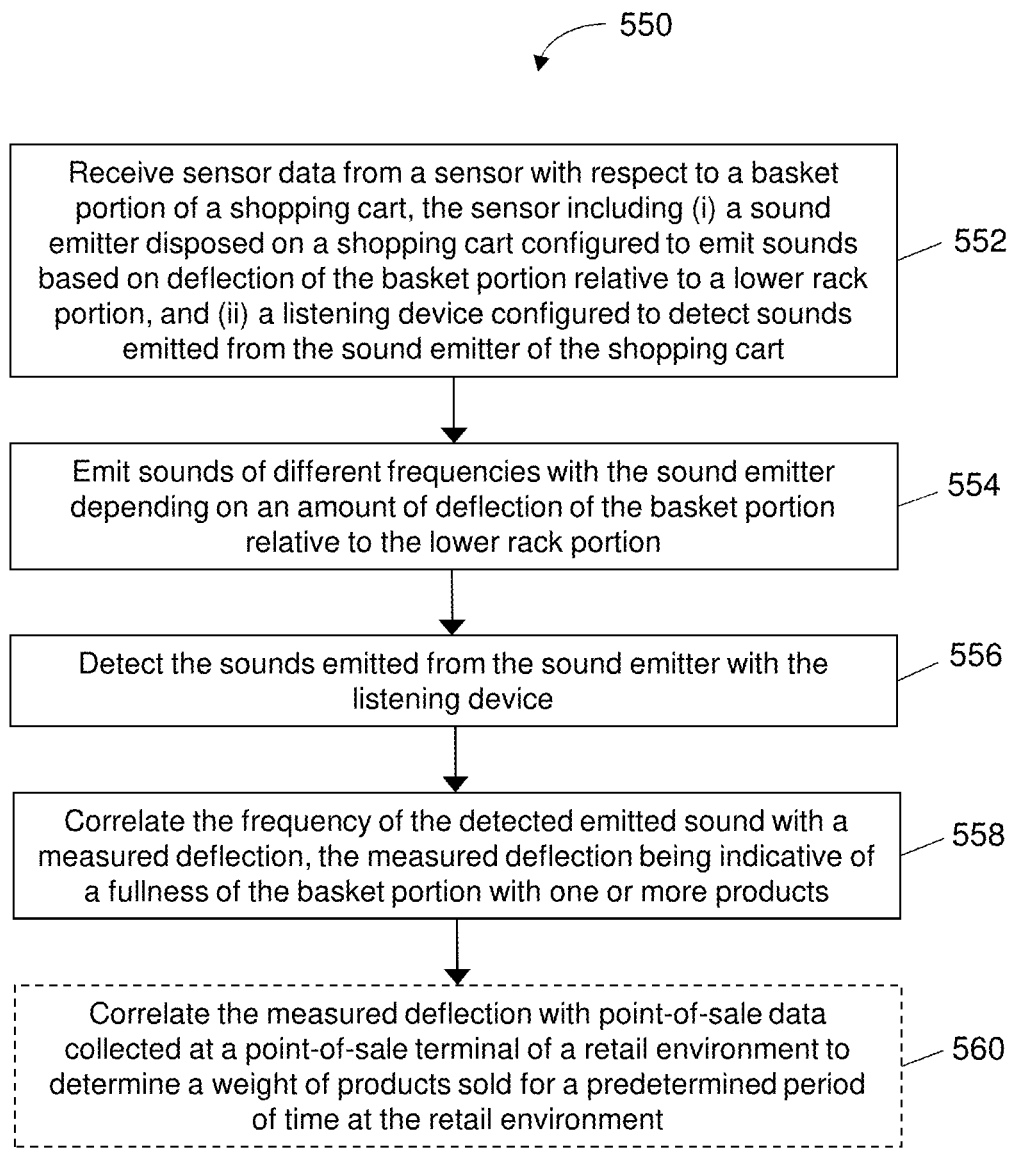
FIG. 12 is a flowchart illustrating an implementation of an exemplary shopping cart deflection measurement system in accordance with an embodiment.

FIG. 12 is a flowchart illustrating an exemplary process 550 as implemented by the shopping cart deflection measurement system 100 including sensors in the form of sound emitters and listening devices. To begin, at step 552, sensor data from a sensor is received, the sensor data corresponding to a basket portion of a shopping cart. The sensor can include a sound emitter and a listening device configured to detect sounds emitted from the sound emitter based on deflection of the basket portion relative to a lower rack portion of the shopping cart. At step 554, sounds of different frequencies can be emitted with the sound emitter affixed on a shopping basket depending on an amount of deflection of the basket portion relative to the lower rack portion. At step 556, the sounds emitted from the sound emitter can be detected with the listening device. At step 558, the frequency of the detected emitted sound can be correlated with a measured deflection, the measured deflection being indicative of a fullness of the basket portion with one or more products. Optionally, at step 560, the measured deflection can be correlated with POS data collected at a POS terminal of the retail environment to determine the weight of products sold for a predetermined period of time at the retail environment.

While exemplary embodiments have been described herein, it is expressly noted that these embodiments should not be construed as limiting, but rather that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the invention.

The invention claimed is:

1. A shopping cart deflection measurement system, comprising:
    a shopping cart including:
        a frame,
        a basket portion pivotably mounted to the frame so as to enable deflection of at least one edge of the basket portion downward in the direction of gravity following a weight being placed in the basket portion, and
        a lower rack portion mounted to the frame and disposed below the basket portion;
    a sensor; and
    a processing device equipped with a processor,
wherein the processing device is configured to execute instructions to measure deflection of the basket portion relative to the lower rack portion of the shopping cart using data acquired by the sensor, the measured deflection being indicative of a fullness of the basket portion with one or more products.

2. The system of claim 1, wherein the sensor includes at least one camera.

3. The system of claim 1, wherein deflection is measured as a change in a distance between a lower surface of the basket portion and an upper surface of the lower rack portion.

4. The system of claim 3, wherein the processing device is configured to execute instructions to:
    measure an initial height between the basket portion and the lower rack portion based on at least one image obtained by the camera prior to a placement of the weight into the basket portion, and
    measure a subsequent height between the basket portion and the lower rack portion based on at least a second image obtained by the camera after the placement of the weight into the basket portion.

5. The system of claim 4, wherein a difference between the subsequent height and the initial height between the basket portion and the lower rack portion corresponds to the deflection of the basket portion relative to the lower rack portion.

6. The system of claim 5, wherein changes in the deflection of the basket portion relative to the lower rack portion are interpreted by the processing device as indicating changes in the weight placed in the basket portion.

7. The system of claim 1, wherein the sensor comprises:
    a sound emitter disposed on the shopping cart configured to emit sounds based on deflection of the basket portion relative to the lower rack portion, and
    a listening device configured to detect sounds emitted from the sound emitter of the shopping cart.

8. The system of claim 7, wherein the sound emitter is mounted to the frame between the basket portion and the lower rack portion.

9. The system of claim 7, wherein the sound emitter is configured to emit sounds of different frequencies depending on an amount of the deflection of the basket portion relative to the lower rack portion.

10. The system of claim 9, wherein the sounds emitted by the sound emitter are outside of human hearing range.

11. The system of claim 9, wherein changes in the frequency of the sounds emitted by the sound emitter correspond to changes in the weight placed in the basket portion.

12. The system of claim 1, wherein the processing device is configured to execute instructions to correlate the measured deflection with point-of-sale data collected at a point-of-sale terminal of a retail environment to determine a weight of products sold for a predetermined period of time at the retail environment.

13. A non-transitory computer-readable medium storing instructions for determining fullness of a shopping cart that are executable by a processing device, the shopping cart including a frame, a basket portion pivotably mounted to the frame so as to enable deflection of at least one edge of the basket portion downward in the direction of gravity following a weight being placed in the basket portion, and a lower rack portion mounted to the frame and disposed below the basket portion, wherein execution of the instructions by the processing device causes the processing device to:
    receive sensor data from a sensor with respect to the basket portion; and
    measure deflection of the basket portion relative to the lower rack portion of the shopping cart based on the sensor data to determine fullness of the basket portion.

14. The medium of claim 13, wherein the sensor includes at least one camera, and wherein execution of the instructions by the processing device causes the processing device to:
- measure an initial height between the basket portion and the lower rack portion based on at least one image obtained by the camera prior to a placement of the weight into the basket portion, and
- measure a subsequent height between the basket portion and the lower rack portion based on at least a second image obtained by the camera after the placement of the weight into the basket portion.

15. The medium of claim 13, wherein the sensor comprises:
- a sound emitter disposed on the shopping cart configured to emit sounds based on deflection of the basket portion relative to the lower rack portion, and
- a listening device configured to detect sounds emitted from the sound emitter of the shopping cart,
- wherein execution of the instructions by the processing device causes the processing device to emit sounds of different frequencies with the sound emitter depending on an amount of the deflection of the basket portion relative to the lower rack portion.

16. The medium of claim 15, wherein execution of the instructions by the processing device causes the processing device to receive the emitted sounds at the listening device and determine the deflection of the basket portion relative to the lower rack portion of the shopping cart based on a frequency of the emitted sounds.

17. The medium of claim 13, wherein execution of the instructions by the processing device causes the processing device to correlate the measured deflection with point-of-sale data collected at a point-of-sale terminal of a retail environment to determine a weight of products sold for a predetermined period of time at the retail environment.

18. A method of determining fullness of a shopping cart, the shopping cart including a frame, a basket portion pivotably mounted to the frame so as to enable deflection of at least one edge of the basket portion downward in the direction of gravity following a weight being placed in the basket portion, and a lower rack portion mounted to the frame and disposed below the basket portion, the method comprising:
- receiving sensor data from a sensor with respect to the basket portion; and
- measuring deflection of the basket portion relative to the lower rack portion of the shopping cart based on the sensor data to determine fullness of the basket portion.

19. The method of claim 18, wherein the sensor includes at least one camera, the method further comprising:
- measuring an initial height between the basket portion and the lower rack portion based on at least one image obtained by the camera prior to a placement of the weight into the basket portion, and
- measuring a subsequent height between the basket portion and the lower rack portion based on at least a second image obtained by the camera after placement of the weight into the basket portion.

20. The method of claim 18, wherein the sensor comprises:
- a sound emitter disposed on the shopping cart configured to emit sounds based on deflection of the basket portion relative to the lower rack portion, and
- a listening device configured to detect sounds emitted from the sound emitter of the shopping cart, and
- wherein the method comprises emitting sounds of different frequencies with the sound emitter depending on an amount of the deflection of the basket portion relative to the lower rack portion.

* * * * *